United States Patent [19]

Yasukawa et al.

[11] Patent Number: 4,528,555
[45] Date of Patent: Jul. 9, 1985

[54] LIGHT EXTINCTION SMOKE DETECTOR

[75] Inventors: Makoto Yasukawa; Kenji Ishii, both of Tokyo, Japan

[73] Assignees: Cerberus AG, Männedorf, Switzerland; Nohmi Bosai Kogyo Co. Ltd., Tokyo, Japan

[21] Appl. No.: 525,036
[22] PCT Filed: Dec. 10, 1982
[86] PCT No.: PCT/EP82/00259
§ 371 Date: Jun. 29, 1983
§ 102(e) Date: Jun. 29, 1983
[87] PCT Pub. No.: WO83/02187
PCT Pub. Date: Jun. 23, 1983

[30] Foreign Application Priority Data

Dec. 11, 1981 [JP] Japan ............... 56-199721

[51] Int. Cl.³ ............................. G08B 17/10
[52] U.S. Cl. ...................... 340/630; 250/573; 356/439
[58] Field of Search ............. 340/630, 629, 628; 250/573, 574; 356/438, 439

[56] References Cited

U.S. PATENT DOCUMENTS 4,185,278  1/1980  Lintelmann et al. ............ 340/630
4,203,100  5/1980  Yamauchi et al. ............... 340/630

FOREIGN PATENT DOCUMENTS 2059128  4/1981  United Kingdom .
2076534  12/1981 United Kingdom .

OTHER PUBLICATIONS

Patent Abstracts of Japan, vol. 2, No. 55, Apr. 21, 1978, p. 1196E78, T. Denki.

Primary Examiner—James L. Rowland
Assistant Examiner—Daniel Myer
Attorney, Agent, or Firm—Werner W. Kleeman

[57] ABSTRACT

A light extinction type smoke detector which uses simple pulsed light or modulation pulsed light to reduce energy consumption, and precisely discriminates smoke generated by fire from extraneous interruption of the light beam from the light source to the photoelectric element to prevent a false alarm.

3 Claims, 8 Drawing Figures

LIGHT EXTINCTION SMOKE DETECTOR

TECHNICAL FIELD

The invention relates to a light extinction smoke detector comprising a light source emitting pulsed light and a light receiver disposed in the path of light from the source so as to receive radiation attenuated by smoke particles in the path of the light. Such smoke detectors are used e.g. as fire alarms.

BACKGROUND ART

In general known light extinction type smoke detectors produce a fire-alarm signal upon detecting the extent to which the output of a photoelectric element receiving light from a light source at the opposite side of a transmission measurement path for smoke is reduced by the smoke of a fire. Therefore, this type of smoke detector has the disadvantage that the interception or interruption of a light path extending from the light source to the photoelectric element, attributable to a shift of the light path or the like, might reduce the output of the photoelectric element and generate a false alarm. The known means for eliminating this disadvantage is described below.

On the output side of the photoelectric element which receives the light from the light source that is spaced or located across a smoke passageway or transmission measurement path, there are connected a first level discriminator which detects a gradual reduction in the output level of the photoelectric element ascribable to the smoke of the fire, and a second level discriminator which detects a rapid or sudden reduction in the output level of the photoelectric element ascribable to an interruption of the light path extending from the light source to the photoelectric element or which detects the rate of variation of such output level. The output of the first level discriminator enters one of the input terminals of a logical product circuit or AND gate through a delay circuit, and the fire-alarm signal is provided by the output terminal of the logical product circuit. The output of the second level discriminator enters the set input terminal of an R/S flip-flop circuit, the output of which enters the other input termminal of the logical product circuit through a "not" or inverter circuit and is also used as a light path interception signal.

Such detection means is unproblematical in a case where the received-light output of the photoelectric element decreases slowly due to the smoke of the fire but does not fall below the second level. However, in a case where high-density smoke initially enters the light path, the output of the photoelectric element falls below the second level and when low-density smoke subsequently enters, causing the output of the photoelectric element to assume a value somewhere between the first and second levels, the output of the second level discriminator enters the input terminal of the logical product circuit through both the R/S flip-flop circuit and the "not" circuit, to inhibit the logical product circuit in providing the fire signal and simultaneously provides the light path interception signal. In addition, when low-density smoke and high-density smoke enter the light path alternatingly, the fire-alarm signal is provided if the output of the photoelectric element is above the second level. However, when the latter output falls below the second level, the second level discriminator produces an output, which inhibits the continuous provision of the fire signal and provides the light path interception signal. It is in this case inevitable that the light path interception signal be produced without the provision of the fire signal, if the delay time of the delay circuit connected to the first level discriminator is longer than the time interval during which the smoke density changes.

DISCLOSURE OF INVENTION

The invention aims at providing a smoke detector which uses simple pulsed light or modulated pulsed light as a light source instead of continuous light in order to reduce energy consumption, and which is capable of avoiding false alarms by correctly detecting and discriminating between smoke generated by a fire and interruption of the light path extending from the light source to the photoelectric element receiving the light. The accompanying drawings, which are incorporated in and constitute a part of this specification, illustrate two exemplary embodiments of the present invention and, together with the specification, serve to explain the principles of the invention.

MODES FOR CARRYING OUT THE INVENTION

Figure 1:
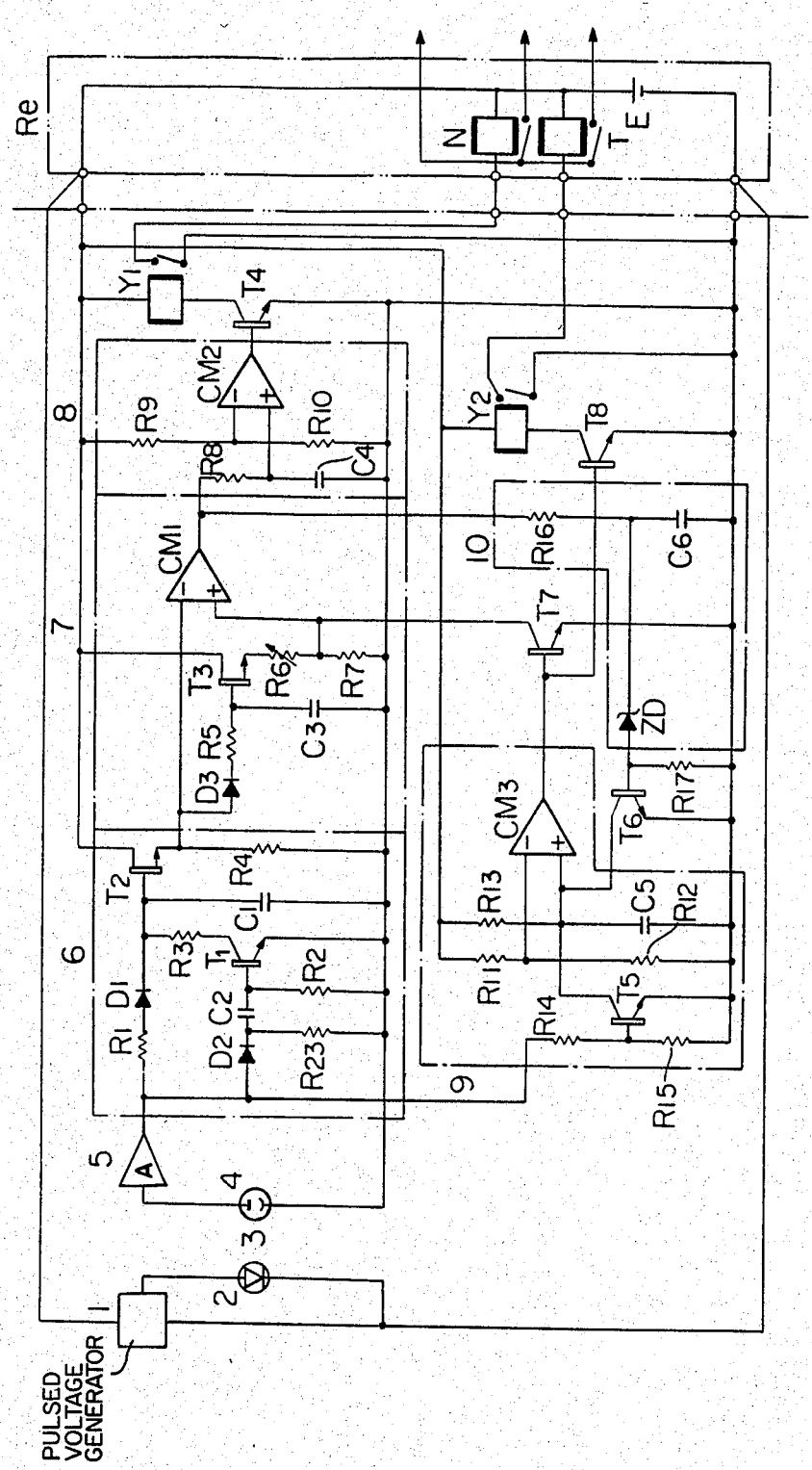
FIG. 1 is a circuit diagram of a first embodiment of the invention.

FIG. 1 is a circuit diagram of a first embodiment of the invention. The reference numeral 1 designates a generator for a simple pulsed voltage, the reference numeral 2 a light-emitting element, such as a light-emitting diode, which emits pulsed light with the output frequency of the generator 1, the reference numeral 3 a space or transmission measurement path through which smoke from a fire passes, the reference numeral 4 a photoelectric element, such as a solar cell, which receives the pulsed light transmitted by the element 2 across the space 3 intervening therebetween, and the reference numeral 5 designates an amplifier for the pulsed voltage developed or induced in the photoelectric element 4. The reference numeral 6 indicates a hold circuit for holding the peak-value of the pulsed voltage, constructed of a circuit which charges a capacitor $C_1$ with the output voltage of the amplifier 5 through a resistor $R_1$ as well as through a diode $D_1$, and a circuit which differentiates the output voltage of the amplifier 5 through a series circuit consisting of a diode $D_2$, a capacitor $C_2$ and a resistor $R_2$ and turns "on" a transistor $T_1$ due to a voltage drop appearing across the resistor $R_2$, so as to discharge the capacitor $C_1$ through a resistor $R_3$ as well as the transistor $T_1$, and which includes a discharging resistor $R_{23}$ for the capacitor $C_2$; and a source follower of a field-effect transistor $T_2$ whose conduction is controlled by the voltage of the capacitor $C_1$ and which includes an output resistor $R_4$. The reference numeral 7 indicates a fire-detection or discriminating circuit which provides a fire-alarm signal when the source voltage of the field-effect transistor $T_2$ of the peak-value hold circuit 6 has reached a predetermined proportion of a reference voltage. It includes a comparator $CM_1$ which has an inverting input terminal (−) supplied with the source voltage of the transistor $T_2$, and which has a noninverting input terminal (+) supplied with the reference voltage appearing at the intermediate junction point of the output resistors $R_6$ and $R_7$ of a source follower of a field-effect transistor $T_3$, the conduction of which is controlled by the voltage of a capacitor $C_3$ that is charged with the source voltage of the transistor $T_2$ through a diode $D_3$ as well as a resistor $R_5$. An output from the comparator $CM_1$ turns "on" transistor $T_4$ with the delay of a predetermined time interval $\tau_1$ through a delay circuit 8 for preventing any erroneous operation due to noise. The delay circuit 8 is constructed of a capacitor $C_4$ which is charged by the aforementioned output of the comparator $CM_1$ through a resistor $R_8$, and a comparator $CM_2$ which has a noninverting input terminal (+) supplied with the voltage of the capacitor $C_4$ and which has an inverting input terminal (−) supplied with a reference voltage at the intermediate junction point of the resistors $R_9$ and $R_{10}$ that are connected in series with each other and with a power source E in a receiver Re. Thus, the delayed output energizes a relay $Y_1$ so as to close its contact $y_1$, whereupon the fire-alarm signal is sent to a zone relay N in the receiver Re so as to operate it. On the other hand, the reference numeral 9 indicates a light-path-interception discriminating circuit. It includes a comparator $CM_3$ whose inverting input terminal (−) is supplied as a reference voltage with the voltage of the intermediate junction point of the resistors $R_{11}$ and $R_{12}$ that are connected in series with each other and with the power source or supply E in the receiver Re, and whose noninverting input terminal (+) is supplied with the voltage of a capacitor $C_5$ that is charged through a resistor $R_{13}$ by the power source or supply E; and a transistor $T_5$ for discharging the capacitor $C_5$, which is connected in parallel with the capacitor $C_5$ and which is turned "on" through resistors $R_{14}$ and $R_{15}$ by the output voltage of the amplifier 5. Normally, the transistor $T_5$ conducts, so that the voltage on the capacitor $C_5$ is null. However, when the light path has been interrupted to drastically lower the output of the amplifier 5 and to render the transistor $T_5$ nonconducting, the capacitor $C_5$ is charged. When, after a predetermined time interval $\tau_2$, the voltage of the capacitor $C_5$ has exceeded the reference voltage of the comparator $CM_3$, this comparator $CM_3$ produces an output signal. When the comparator $CM_3$ produces the output signal, a transistor $T_7$ turns "on" to make the voltage of the noninverting input terminal (+) of the comparator $CM_1$ in the fire-detection or discriminating circuit 7 null or zero, and the operation of the fire-detection circuit 7 is inhibited. At the same time, a transistor $T_8$ turns "on", and a relay $Y_2$ is energized to close its contact $y_2$ and to send a light-path-interruption signal, which operates a light-path-interruption indicating relay T in the receiver Re. Conversely, when the comparator $CM_1$ has produced its output signal, a transistor $T_6$ which has a resistor $R_{17}$ connected across the base and emitter thereof is turned "on" after a time interval $T_3$ determined by a delay circuit 10, which is constructed of a capacitor $C_6$ that is charged by the output voltage of the comparator $CM_1$ through a resistor $R_{16}$ and a Zener diode ZD that is turned "on" by the voltage of the capacitor $C_6$. Thus, the voltage of the noninverting input terminal (+) of the comparator $CM_3$ is made null or zero, and the operation of the light-path-interruption discriminating circuit 9 is interdicted or inhibited.

Figure 2:
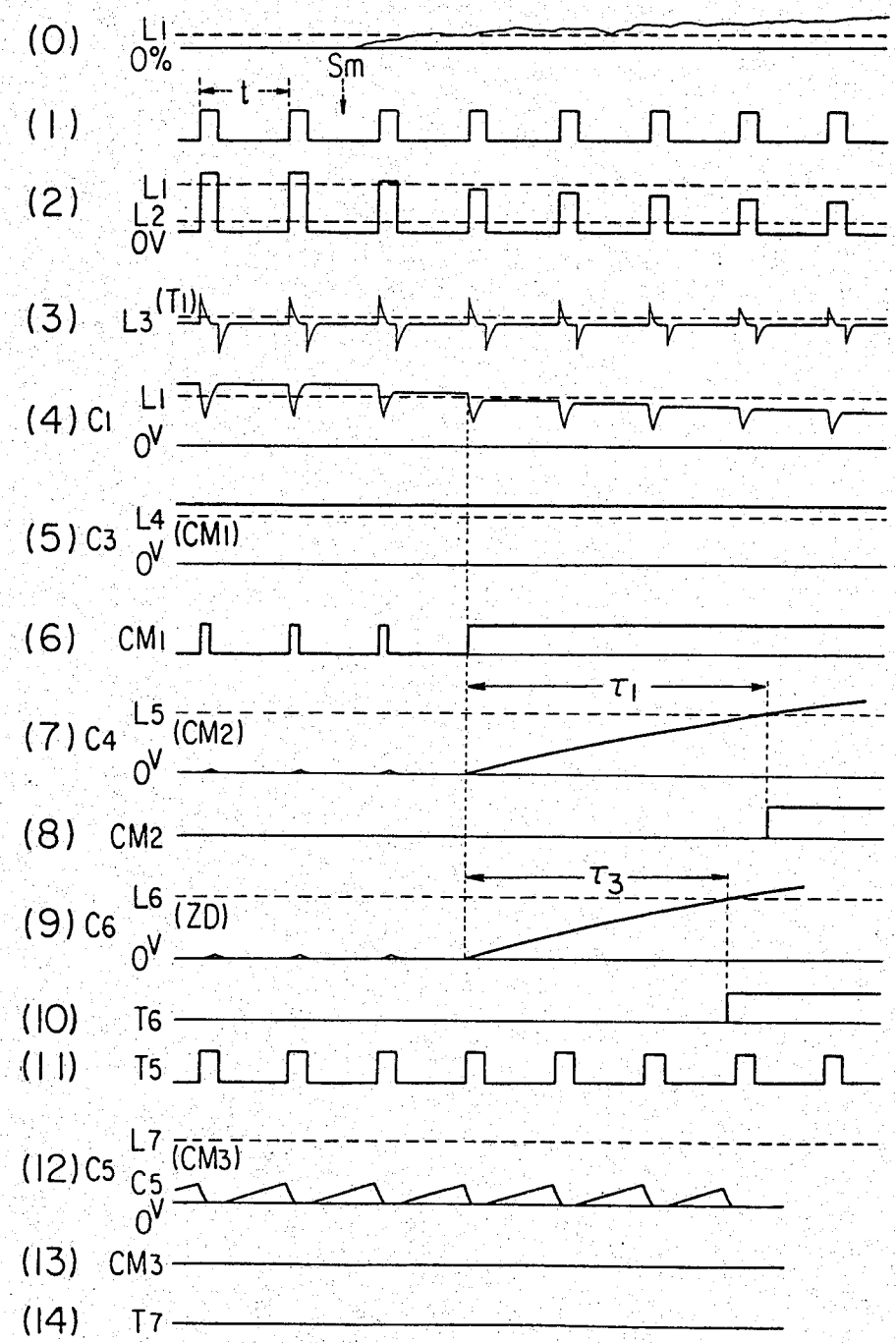
FIGS. 2 and 3 are timing charts or diagrams showing the operating states of various components of the embodiment shown in FIG. 1.
Figure 3:
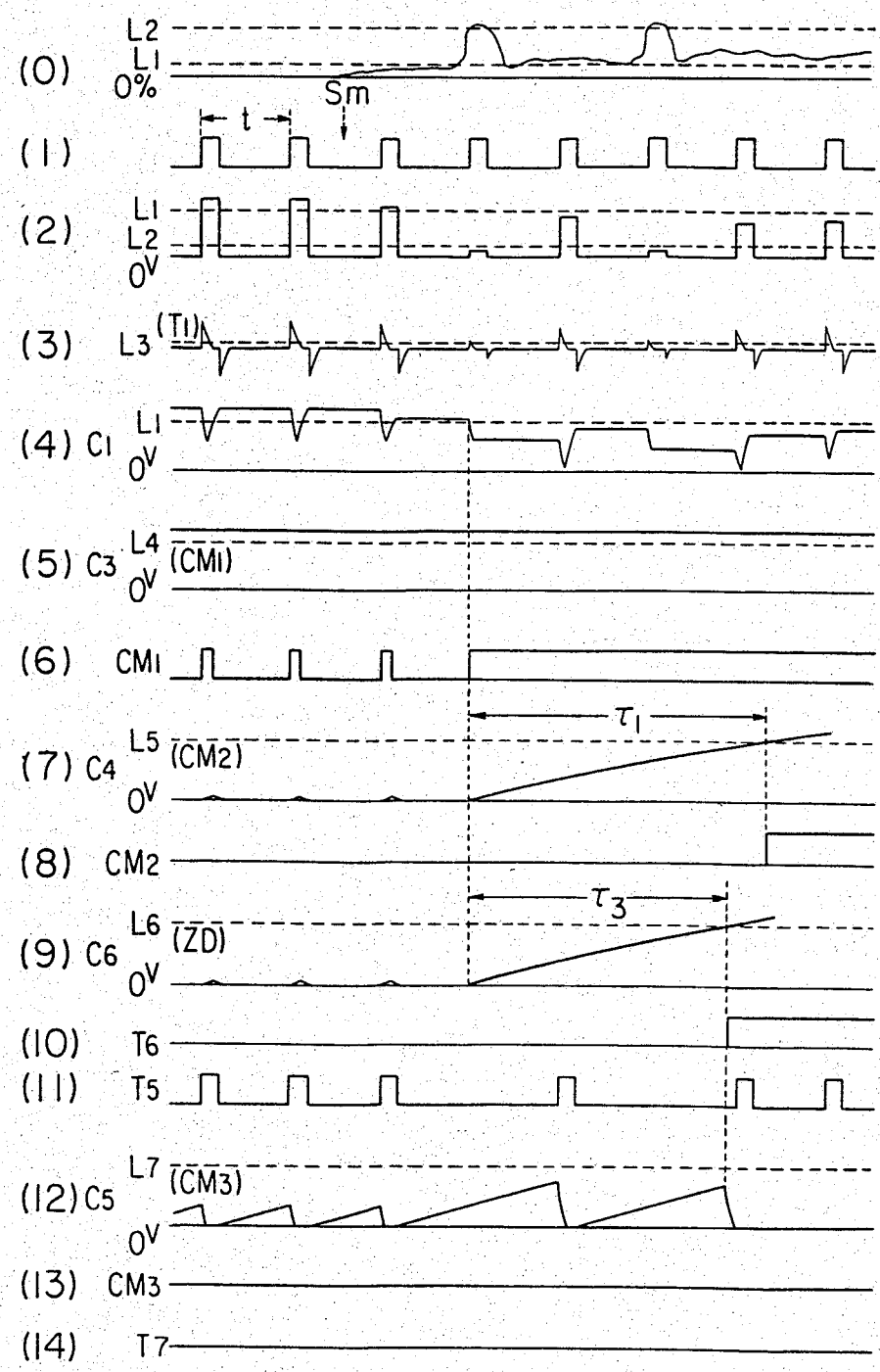
Figure 4:
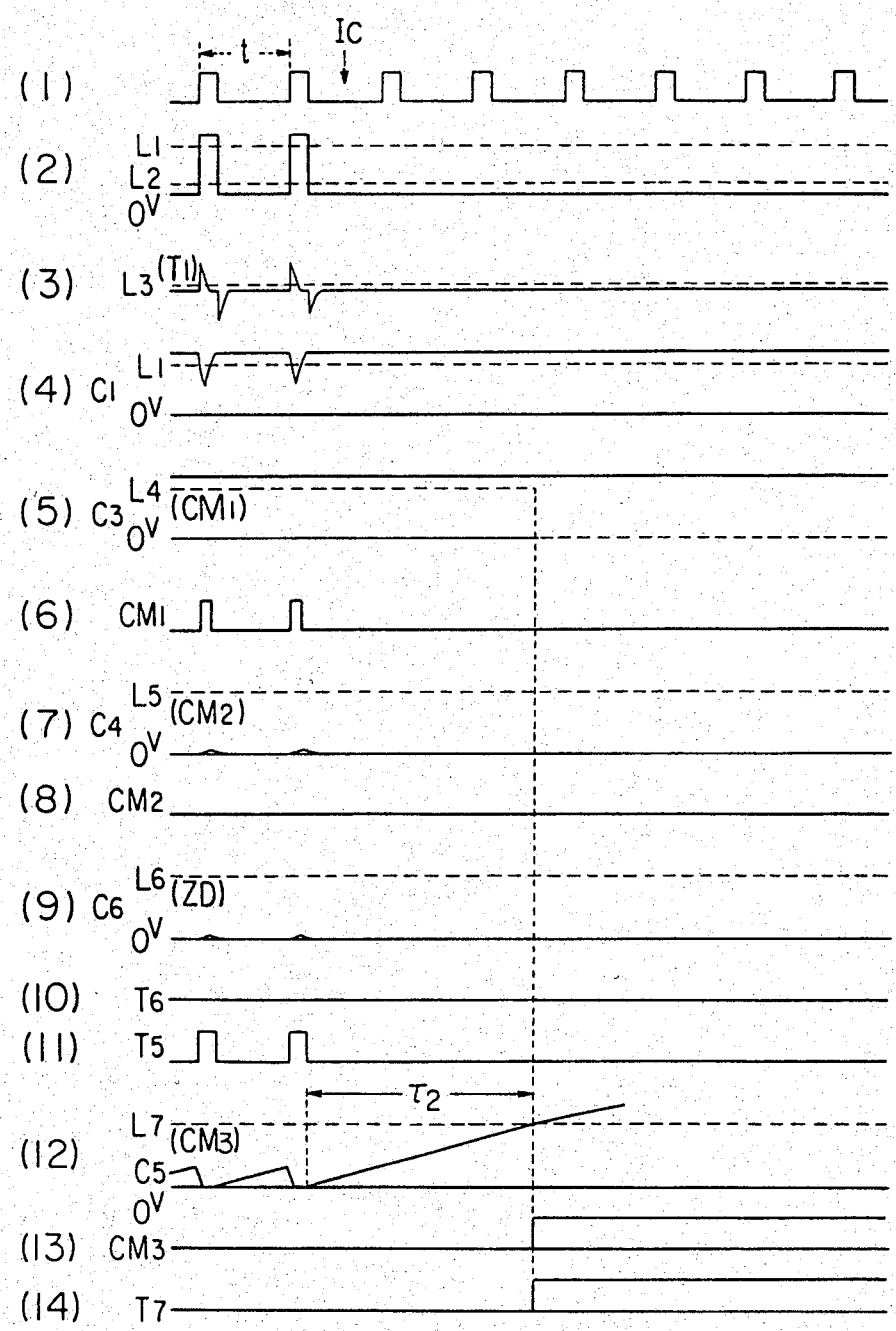
FIGS. 4 and 5 are timing charts or diagrams showing the operating states of various components in the cases where interruption of the light path has occured.
Figure 5:
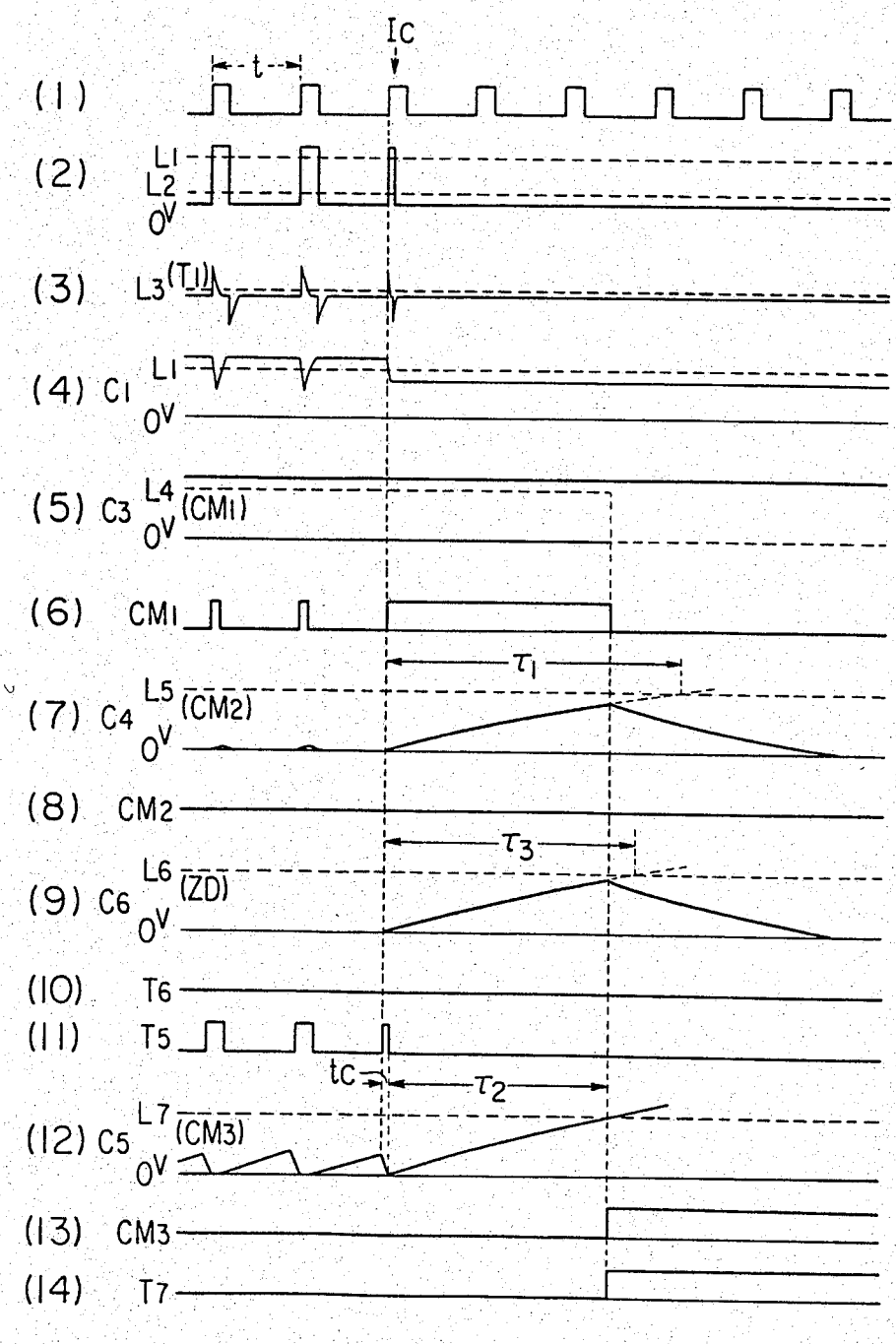

FIGS. 2 and 3 are timing charts or diagrams respectively showing the operating states of various components in the cases where smoke has entered the light path at points of time indicated by arrows Sm and the normal states as shown at (0). In the former case, i.e. that of FIG. 2, the density of the smoke has changed slowly as indicated in solid line, while in the latter case, i.e. that of FIG. 3, the high-density smoke equal to or above a light-path-interruption level has entered initially, followed by the low-density smoke equal to or above a fire level. FIGS. 4 and 5 are timing charts or diagrams respectively showing the operating states of various components in the cases where the interruption of the light path has occurred at points of time indicated by arrows Ic in the normal states. In the timing charts or diagrams of FIGS. 2 to 5, (0) illustrates the density variation of the smoke in the light path, (1) the pulsed light emission output of the light-emitting element 2 having a period t, (2) the output of the amplifier 5 obtained by amplifying the light reception or received-light output voltage of the photoelectric element 4, (3) the voltage obtained by differentiating the output voltage of the amplifier 5, the illustrated voltage appearing across the resistor $R_2$ of the peak-value hold circuit 6, (4) the peak voltage held in the capacitor $C_1$, (5) the maximum value of the output voltage of the amplifier 5, the illustrated value being stored in the capacitor $C_3$ of the fire-detection or discriminating circuit 7, (6) the output of the comparator $CM_1$, (7) the voltage of the capacitor $C_4$ of the delay circuit 8, (8) the output of the comparator $CM_2$, (9) the voltage of the capacitor $C_6$ of the delay circuit 10, (10) the operating state of the transistor $T_6$, (11) the operating state of the transistor $T_5$ of the light-path-interruption discriminating circuit 9, (12) the voltage of the capacitor $C_5$, (13) the output of the comparator $CM_3$, and (14) the operating state of the transistor $T_7$. Symbol $L_1$ at (0), (2) and (4) in FIGS. 2 to 5 denotes the level which is to be considered to represent a fire, symbol $L_2$ at (0) and (2) denotes the level which is to be considered to represent a light-path-interruption, symbol $L_3$ at (3) denotes that level of the base-emitter voltage of the transistor $T_1$ which is necessary for this transistor to conduct, symbol $L_4$ at (5) denotes the level of the reference voltage which is applied to the noninverting input terminal (+) of the comparator $CM_1$ and which corresponds to the fire level $L_1$ at (2) and (4), symbol $L_5$ at (7) denotes the level of the reference voltage which is applied to the inverting input terminal (−) of the comparator $CM_2$, symbol $L_6$ at (9) denotes the level of the Zener voltage of the Zener diode ZD, and symbol $L_7$ at (12) denotes the level of the reference voltage which is applied to the inverting input terminal (−) of the comparator $CM_3$.

Referring to FIGS. 2 to 5, while there is no smoke in the smoke passage or transmission measurement path 3 and the light path is also not interrupted, the differentiated voltage of the output voltage of the amplifier 5 as shown at (3) appears across the resistor $R_2$ each time the amplifier output voltage shown at (2) develops, so that the transistor $T_1$ turns "on" to discharge the capacitor $C_1$ through the resistor $R_3$ as shown at (4). However, when the above differentiated voltage below the level $L_3$, the transistor $T_1$ turns "off", so that the capacitor $C_1$ is recharged to the output voltage of the amplifier 5 and holds the peak-value thereof. The held voltage is applied to the inverting input terminal (−) of the comparator $CM_1$ of the fire-detection or discriminating circuit 7. This voltage held by the capacitor $C_1$ momentarily falls below the fire level $L_1$, as accordingly does the level $L_4$ of the reference voltage of the noninverting input terminal (+) of the comparator $CM_1$ of the fire-detection or discriminating circuit 7 as shown at (5), when the transistor $T_1$ has turned "on". Therefore, the comparator $CM_1$ produces its output as shown at (6), and the capacitors $C_4$ and $C_6$ are charged by the output of the comparator $CM_1$ as shown at (7) and (9) respectively. However, since the output of the comparator $CM_1$ ceases immediately, the voltages of the capacitors $C_4$ and $C_6$ do not reach the level $L_5$ of the reference voltage of the comparators $CM_2$ and the level $L_6$ of the Zener voltage of the Zener diode ZD respectively, so that these capacitors $C_4$ and $C_6$ are discharged through the comparator $CM_1$. On the other hand, the capacitor $C_5$ of the light-path-interruption discriminating circuit 9 is charged through the resistor $R_{13}$. However, each time the output of the amplifier 5 exceeds the light-path-interruption level $L_2$ as shown at (2), the transistor $T_5$ turns "on" as shown at (11), and the capacitor $C_5$ is discharged through the transistor $T_5$ as shown at (12), so that the voltage of the capacitor $C_5$ does not reach the level $L_7$ of the reference voltage applied to the inverting input terminal (−) of the comparator $CM_3$.

When, as illustrated at (0) in FIG. 2, smoke has started entering the light path at the time indicated by the arrow Sm and the density of the smoke slowly changes as indicated in solid line, the output voltage of the amplifier 5 falls gradually with increase in the density of the smoke as shown at (2), and the differentiated voltage thereof shown at (3) falls gradually accordingly. Each time the differentiated voltage exceeds the level $L_3$, the transistor $T_1$ turns "on" to discharge the capacitor $C_1$ as shown at (4), and the discharged capacitor $C_1$ is recharged up to the peak-value of the lowered output voltage of the amplifier 5, but as the output voltage of the amplifier 5 has fallen below the level $L_1$ at (2), the voltage held by the capacitor $C_1$ falls below the level $L_1$, and the input of the inverting input terminal (−) of the comparator $CM_1$ falls below the reference voltage $L_4$ of the noninverting input terminal (+), so that the comparator $CM_1$ continues to provide its output as shown at (6). As a result, the capacitors $C_4$ and $C_6$ are charged by the output of the comparator $CM_1$ through the resistors $R_8$ and $R_{16}$, respectively as shown at (7) and (9). On the other hand, the capacitor $C_5$ is charged through the resistor $R_{13}$ as shown at (12), just as in a normal state. However, since the output of the amplifier 5 is higher than the light-path-interruption level $L_2$ as shown at (2), the transistor $T_5$ turns "on" as shown at (11) and discharges the capacitor $C_5$ each time the amplifier 5 provides its output. As shown at (9), the voltage of the capacitor $C_6$ increases and exceeds the level $L_6$ corresponding to the Zener voltage of the Zener diode ZD after the predetermined time interval $\tau_3$. Then, the transistor $T_6$ turns "on" as shown at (10) and inhibits the comparator $CM_3$ from providing the output. Subsequently, the voltage of the capacitor $C_4$ increases as shown at (7) and exceeds the level $L_5$ of the reference voltage of the inverting input terminal (−) of the comparator $CM_2$ after the predetermined time interval $\tau_1$. Then, the comparator $CM_2$ provides its output as shown at (8), the transistor $T_4$ is turned "on", and the relay $Y_1$ operates to close its contact $y_1$, so that the fire-alarm signal is provided.

Next, when, as illustrated at (0) in FIG. 3, smoke has started entering the light path at the time indicated by the arrow Sm and high-density smoke equal to or above the light-path-interruption level $L_2$ has initially entered as indicated in solid line, the output of the amplifier 5 immediately falls below the light-path-interruption level $L_2$ as shown at (2), and the transistor $T_5$ of the light-path-interruption discriminating circuit 9 does not turn "on", as shown at (11), so that the capacitor $C_5$ continues to charge as shown at (12). However, when low-density smoke between the fire level $L_1$ and the light-path-interruption level $L_2$ subsequently enters, the output of the amplifier 5 becomes a value somewhere between the levels $L_1$ and $L_2$ as shown at (2), and the transistor $T_5$ turns "on" again as shown at (11), so that the capacitor $C_5$ discharges as shown at (12). Therefore, in a case where the output of the amplifier 5 has fallen below the light-path-interruption level $L_2$ for a short time, the comparator $CM_3$ of the light-path-interruption discriminating circuit 9 does not provide its output, as illustrated at (13). As shown at (7) and (9), the respective capacitors $C_4$ and $C_6$ of the delay circuits 8 and 10 start being charged by the output of the comparator $CM_1$ of the fire-detection or discriminating circuit 7 illustrated at (6), at which time the output of the amplifier 5 has fallen below the fire level $L_1$ as shown at (2). When, as illustrated at (9), the voltage of the capacitor $C_6$ has reached the level $L_6$ of the Zener voltage of the Zener diode ZD after the predetermined time interval $\tau_3$, the transistor $T_6$ turns "on" as shown at (10), to inhibit the operation of the light-path-interruption discriminating circuit 9. When, as illustrated at (7), the voltage of the capacitor $C_4$ has exceeded the level $L_5$ of the reference voltage applied to the inverting input terminal (−) of the comparator $CM_2$ of the delay circuit 8, after the predetermined time interval $\tau_1$, the comparator $CM_2$ provides its output as shown at (8), the transistor $T_4$ turns 2 "on", and the relay $Y_1$ operates to close its contact $y_1$, so that the fire-alarm signal is provided.

As can be seen from such operating states, according to the invention, in both cases where smoke of a higher density than the light-path-interruption level has entered the light path initially and then smoke of a density somewhere between the fire level $L_1$ and the light-path-interruption level $L_2$ has entered, and where smoke of such high and low densities has entered alternately, the capacitor $C_5$ of the light-path-interruption discriminating circuit 9 discharges as shown at (12), when thin smoke somewhere between the levels $L_1$ and $L_2$ has entered. Therefore, the comparator $CM_3$ does not provide its output.

FIG. 4 illustrates the operating states of the various components in the case where the light path has been interrupted during quiescent period of the light-emission of the light emitting element 2. The arrow Ic denotes the time at which the interruption has occurred. Notwithstanding that the light-emitting element 2 continues to emit pulsed light as shown at (1), the amplifier 5 produces, as shown at (2), no output after the time indicated by the arrow Ic, because the photoelectric element 4 receives no light. As a result, the differentiated voltage of the amplifier output does not appear across the resistor $R_2$, and the capacitor $C_1$ continues to hold the peak voltage of the last output of the amplifier 5, as shown at (4). Since the comparator $CM_1$ does not produce its output either, as shown at (6), the capacitors $C_4$ and $C_6$ are no longer charged, as shown at (7) and (9), respectively. On the other hand, the capacitor $C_5$ of the light-path-interruption dicriminating circuit 9 is charged through the resistor $R_{13}$ as shown at (12). Herein, since the transistor $T_5$ has turned "off" due to the null output of the amplifier 5, the capacitor $C_5$ continues to charge. After the time interval $\tau_2$, the charged voltage of the capacitor $C_5$ exceeds the level $L_7$ of the reference voltage of the inverting input terminal (−) of the comparator $CM_3$, and this comparator $CM_3$ provides its output as shown at (13). Therefore, the transistor $T_7$ turns "on" as shown at (14) and makes the level $L_4$ of the reference voltage of the noninverting input terminal (+) of the comparator $CM_1$ null as shown at (5), so as to inhibit the comparator $CM_1$ from providing its output. Simultaneously, the transistor $T_8$ turns "on" to energize the relay $Y_2$ so as to close the contact $y_2$ thereof and to provide the light-path-interruption signal.

FIG. 5 illustrates the operating states of the various components in the case where the light path has been interrupted at the time indicated by the arrow Ic, during active light emission of the light-emitting element 2. At this time, the time interval during which the photoelectric element receives the light is short on account of the interruption of the light path. The width of the output voltage of the amplifier 5 narrows as shown at (2), the differentiated voltage of the amplifier output appearing across the resistor $R_2$ is sharp, and the conduction interval of the transistor $T_1$ is short as compared with that in the normal state. In the short interval, the capacitor $C_1$ is discharged, and the charged voltage thereof falls below the fire level $L_1$ of the comparator $CM_1$ as shown at (4). The the capacitor $C_1$, after discharge, can scarcely be charged with such a narrow pulse width voltage of the amplifier 5. Since the lowered voltage held by the capacitor $C_1$ has fallen below the level $L_4$ of the reference voltage of the noninverting input terminal (+) of the comparator $CM_1$ corresponding to the fire level $L_1$, the comparator $CM_1$ produces its output as shown at (6), and the capacitors $C_4$ and $C_6$ are charged by this output as shown at (7) and (9) respectively. On the other hand, since the pulse width of the output voltage of the amplifier 5 is so narrow that the transistor $T_5$ turns on for a short time only as shown at (11), charge of the the charge of the capacitor $C_5$ discharges as shown at (12). Immediately after completion of discharge, the capacitor $C_5$ begins to recharge. When, after the time interval $\tau_2$, the voltage of the capacitor $C_5$ has exceeded the level $L_7$ of the reference voltage applied to the inverting input terminal (−) of the comparator $CM_3$, this comparator $CM_3$ produces its output as shown at (14). Then, the level $L_4$ of the reference voltage of the noninverting input terminal (+) of the comparator $CM_1$ becomes null as shown at (5), and the output of the comparator $CM_1$ becomes null as shown at (6), so that the capacitors $C_4$ and $C_6$ are discharged through the comparator $CM_1$ as shown at (7) and (9) respectively. At the same time, the output of the comparator $CM_3$ turns "on" the transistor $T_8$, which energizes the relay $Y_2$ to close the contact $y_2$, so that the light-path-interruption signal is provided. The relationships of the magnitudes of the time intervals $\tau_1$, $\tau_2$ and $\tau_3$ may be selected as the following inequalities where $t_c$ denotes the conduction time or interval of the transistor $T_5$ corresponding to the pulse width of the pulse output shown at (2) and obtained by amplifying the received-light output of the photoelectric element 4:

$$\tau_1 - t_c > \tau_2,\ \tau_3 - t_c > \tau_2,\ \tau_3 \leq \tau_1$$

The reasons therefor are stated below. When interruption of the light path has occurred during active light emission of the light-emitting element 2 as illustrated at (1) in FIG. 5, the comparator $CM_1$ of the fire-detection or discriminating circuit 7 produces its output continuously from the time of initiation of the light emission, as seen from (6), and the capacitors $C_4$ and $C_6$ begin to charge as shown at (7) and (9) respectively. In addition, as seen from (12), the capacitor $C_5$ having begun to at the time of the light-path-interruption, which time is later than the time of initiation of charging of the capacitors $C_4$ and $C_6$ equal to the conduction time $t_c$ of the transistor $T_5$, continues to charge. Therefore $\tau_2$ must be shorter than the time interval obtained by subtracting $t_c$ from $\tau_1$ or $\tau_3$, in order that the light-path-interruption signal may be provided before the generation of the fire-alarm signal and the inhibition of the operation of the light-path-interruption discriminating circuit. Moreover, the light-path-interruption signal must not be provided before the fire-alarm signal is produced. Therefore, $\tau_3$ must not be longer than $\tau_1$.

Figure 6:
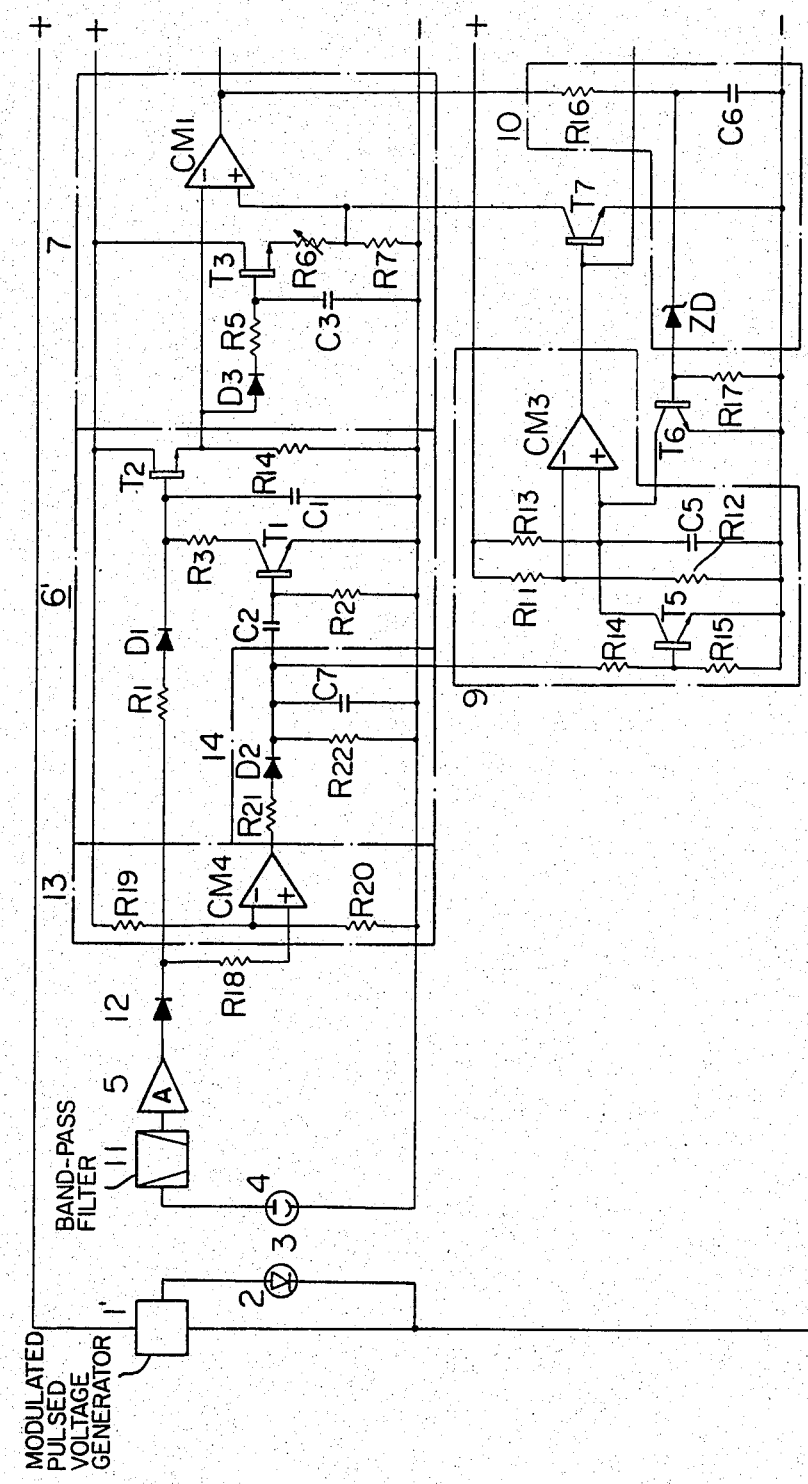
FIG. 6 is a circuit diagram of the essential portions of a second embodiment of the invention.
Figure 7:
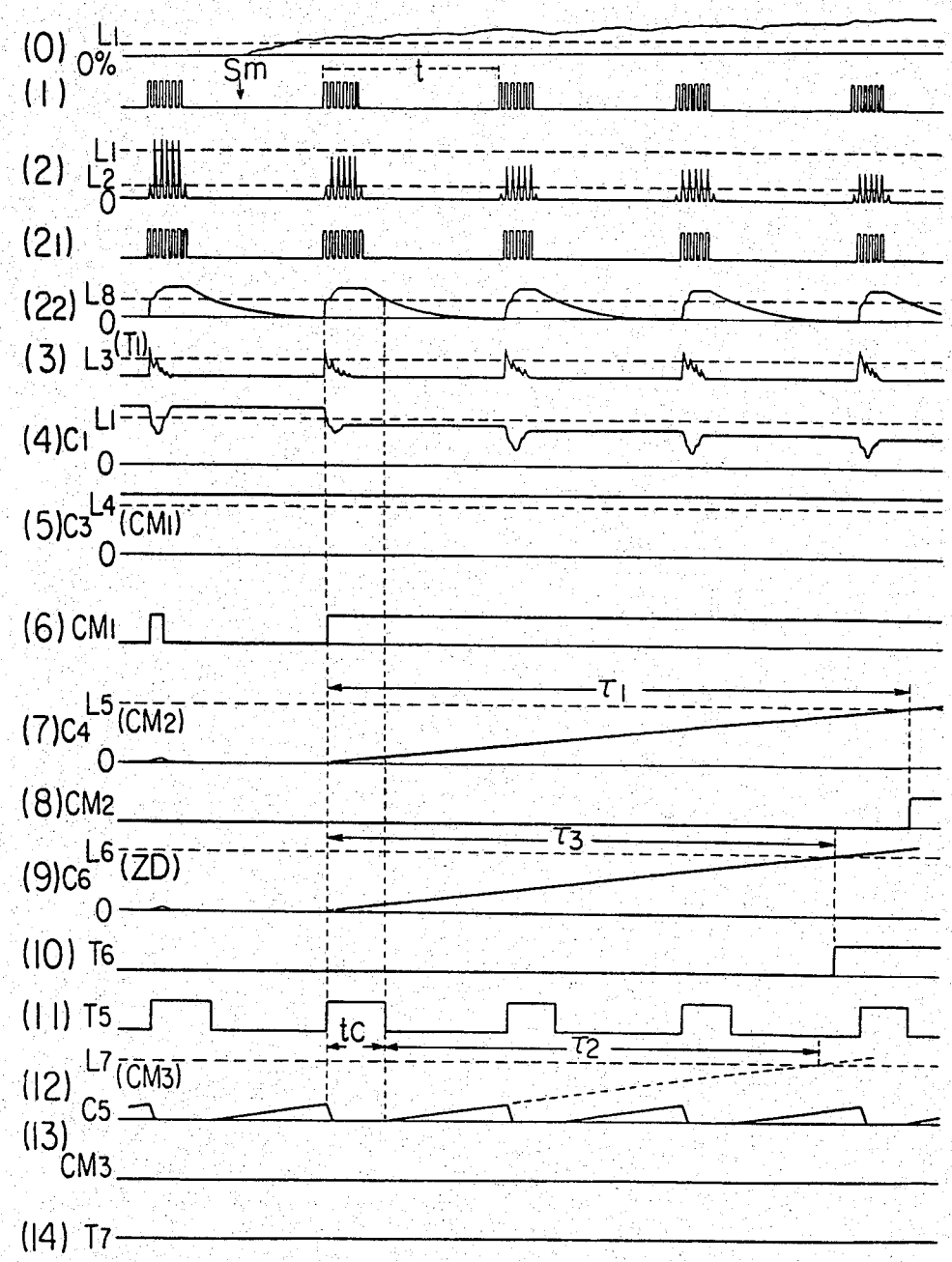
FIGS. 7 and 8 are timing charts or diagrams corresponding to FIGS. 2 and 4 and showing the operating states of various components of the embodiment shown in FIG. 6.

FIG. 6 is a circuit diagram of the essential components of a second embodiment of the invention which employs modulated pulsed light shown at (1) in FIG. 7, which is a timing chart or diagram corresponding to FIG. 2. As compared with the first embodiment of the invention shown in FIG. 1, the second embodiment of the invention differs only in that a generator 1′ for the modulated pulsed voltage is employed instead of the generator 1 for the simple pulsed voltage, that a band-pass filter 11 which passes only current of a modulation pulsed frequency based on a modulated pulsed voltage having developed in the photoelectric element 4 for receiving the light, and a half-wave rectifier circuit 12 which rectifies the output of the amplifier 5, are respectively disposed before and after the amplifier 5 for the output voltage of the element 4, and that a peak-value-hold circuit 6′ is employed instead of the peak-value-hold circuit 6. The components corresponding to those on the right side in FIG. 1 have been omitted in FIG. 6. More specifically, in the circuit 6, the output voltage of the amplifier 5 is differentiated through the series circuit consisting of the diode $D_2$, capacitor $C_2$ and resistor $R_2$, and the transistor $T_1$ is turned "on" by the voltage drop appearing across the resistor $R_2$. In contrast, the circuit 6′ includes a waveshaping circuit 13 wherein the output voltage of the half-wave rectifier circuit 12 shown at (2) in FIG. 7 is applied through a resistor $R_{18}$ to the noninverting input terminal (+) of a comparator $CM_4$, to the inverting input terminal (−) of which is coupled the intermediate point of resistors $R_{19}$ and $R_{20}$ connected in series to the same power source as that E in the receiver Re shown in FIG. 1, and wherein the aforementioned output voltage is waveshaped through the comparator $CM_4$ as shown at $(2_1)$ in FIG. 7; and a charge-and-discharge circuit 14 for the output of the circuit 13, wherein as shown at $(2_2)$ in FIG. 7, a capacitor $C_7$ is once charged with the output of the circuit 13 through a resistor $R_{21}$ as well as a diode $D_2$, and the charges of the capacitor $C_7$ are discharged through a discharge resistor $R_{22}$ before the circuit 13 provides the next output thereof. The output voltage of the circuit 14, namely, the voltage of the capacitor $C_7$ shown at $(2_2)$ in FIG. 7 is differentiated through the series circuit consisting of the capacitor $C_2$ and the resistor $R_2$, as shown at (3) in FIG. 7, and the transistor $T_1$ is turned "on" by the voltage drop appearing across the resistor $R_2$. Both the embodiments agree in the point that the conduction of the transistor $T_5$ of the light-path-interruption discriminating circuit is controlled by the voltage of the input side of the differentiation circuit which has the capacitor $C_2$ and the resistor $R_2$ connected in series.

Figure 8:
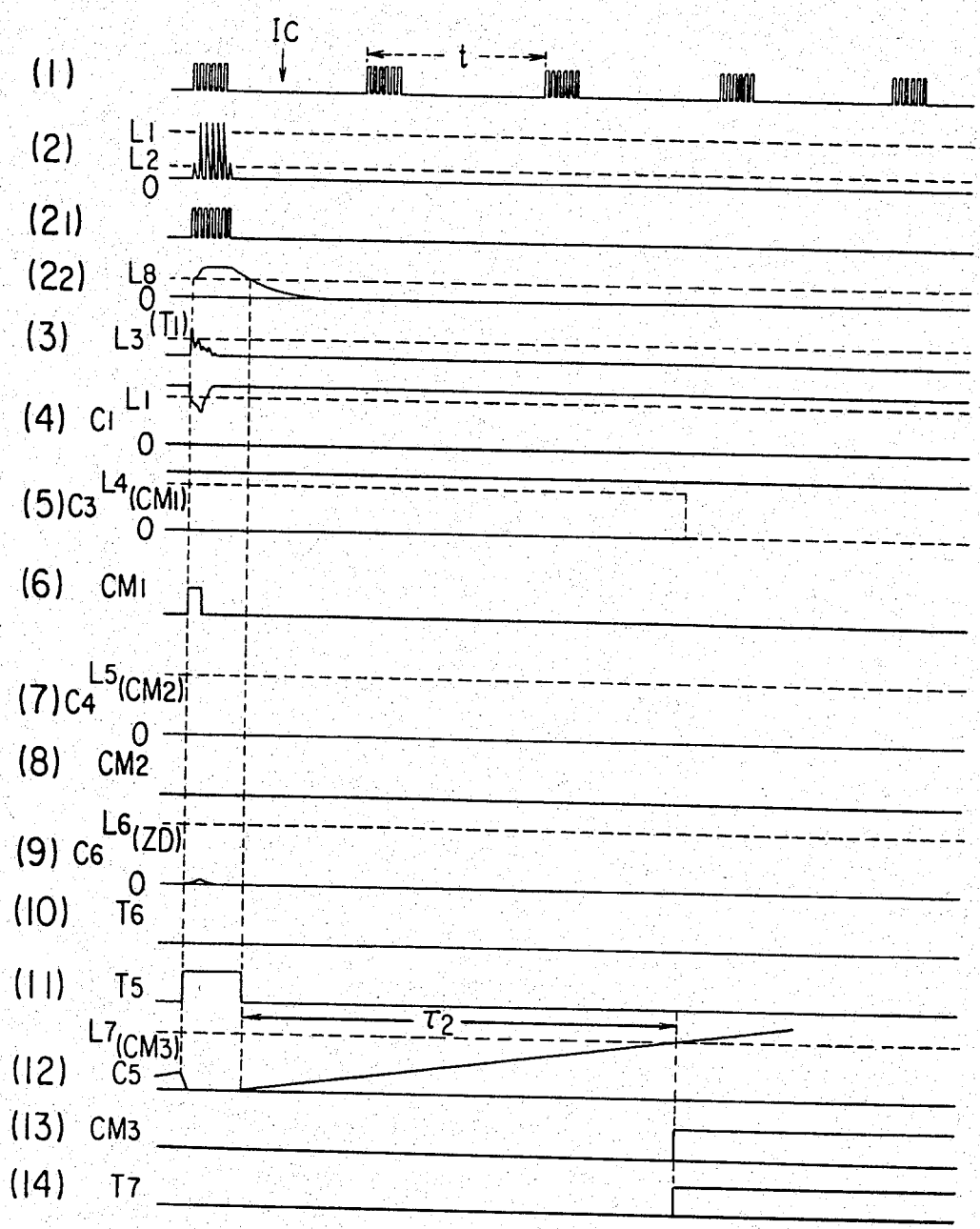

FIGS. 7 and 8 are time charts corresponding to FIGS. 2 and 4 and showing the operating states of various parts as to the embodiment shown in FIG. 6, in the case where smoke has entered the light path in the normal state at a point of time indicated by arrow Sm and where the smoke density has changed slowly, and in the case where the interruption of the light path has occurred in the normal state at a point of time indicated by arrow Ic, respectively. In these time charts, (0) illustrates the density variation of the smoke in the light path, (1) the modulated pulse light emission of the light emitting element 2 having a period t, (2) the output voltage obtained from the received light output of the photoelectric element 4 passing through the band pass filter 11, amplifier 5 and half-wave rectifier circuit 12, ($2_1$) the output voltage of the waveshaping circuit 13 in the peak value holding circuit 6', ($2_2$) the output voltage of the charge-and-discharge circuit 14 in the same 6', (3) the voltage appearing across the resistor $R_2$ of the circuit 6' i.e. a result of the differentiation of the output voltage of the circuit 14, (4) the peak voltage of each pulse train of the half-wave rectifier circuit 12, this peak voltage being held in the capacitor $C_1$, (5) the maximum value in the output voltages of the circuit 12, this value being stored in the capacitor $C_3$ of the fire discriminating circuit 7, (6) the output of the comparator $CM_1$, (7) the voltage of the capacitor $C_4$ of the delay circuit 8 shown in FIG. 1 and connected on the output side of the comparator $CM_1$, (8) the output of the comparator $CM_2$ of the same circuit as the circuit 8 shown in FIG. 1, (9) the voltage of the capacitor $C_6$ of the delay circuit 10, (10) the operating state of the transistor $T_6$, (11) the operating state of the transistor $T_5$ of the light-path-interruption-discriminating circuit 9, (12) the voltage of the capacitor $C_5$, (13) the output of the comparator $CM_3$, and (14) the operating state of transistor $T_7$. Symbol $L_1$ at (0), (2) and (4) denotes the level which is to be determined a fire, symbol $L_2$ at (2) denotes the level which is to be determined light-path-interruption, the levels indicated by $L_3$-$L_7$ at (3)–(12) are the same as those shown in FIGS. 2 and 4, and symbol $L_8$ at ($2_2$) denotes the voltage level which is required for the conduction of the transistor $T_5$ of the light-path-interruption-discriminating circuit 9.

In this manner, in the embodiment shown in FIG. 6, the modulated pulse light of high frequency is used instead of the simple pulse light, and the output voltage of the light receiving photoelectric element 4 is passed through the band-pass filter 11, amplified by the amplifier 5 and rectified by the half-wave rectifier circuit 12. Therefore, due to inductance, resistance etc. in the filter 11 and the amplifier 5, the amplitude of the rectified output voltage becomes smaller at the end parts thereof as seen at (2) and in FIGS. 7 and 8, and there is a fear that the smoke detector might operate erroneously, (refer to the specification and drawings of Japanese Utility Model Application No. 56-139190 filed by the same Applicant). For this reason, the output waveform is shaped as shown at ($2_1$) by means of the wave-shaping circuit 13 in the peak value holding circuit 6'. The capacitor $C_7$ of the charge-and-discharge circuit 14 is charged with the shaped output voltage through the resistor $R_{21}$ and the diode $D_2$ as illustrated at ($2_2$). Each time a charging current flows through the capacitor $C_7$, the voltage shown at (3) develops which is the differentiated voltage of the capacitor $C_7$ across the resistor $R_2$ through the capacitor $C_2$. Only when the peak value of the voltage has exceeded the level $L_3$, the transistor $T_1$ turns "on" to discharge the charges of the capacitor $C_1$ as shown at (4). After the end of the discharge, the capacitor $C_1$ is recharged with the output voltage of the half-wave rectifier circuit 12 shown at (2), until the voltage of this capacitor reaches the peak value of the output voltage shown at (2) of each figure. Except for these points, the operating states do not differ from those of the various portions of the embodiment of FIG. 1 as illustrated in FIGS. 2 and 4. In addition, the operating states of the various portions of the embodiment of FIG. 6, corresponding to those in the embodiment of FIG. 1, in the case shown in FIG. 3 where high density smoke equal to or above the light path interception level has entered the light path at first and where low density smoke equal to or above the fire level has subsequently entered and in the case shown in FIG. 5 where the interruption of the light path has occurred at a point of time indicated by the arrow Ic during the light emission of the light emitting element 2, can be readily conjectured from the operating states of the various portions shown in FIGS. 7 and 8 because the parts ($2_2$) of FIGS. 7 and 8 correspond to the parts (2) of FIGS. 2–5. Regarding the relationships of length among the periods of time $\tau_1$, $\tau_2$ and $\tau_3$, the embodiment of FIG. 6 is the same as that of FIG. 1, except in the point that $t_c$ denotes the conduction time of the transistor $T_5$ which is determined by the waveform of the output voltage of the charge-and-discharge circuit 14 shown at ($2_2$), corresponding to the width of the pulse train equal to or above the level $L_2$ of the half-wave rectified output shown at (2) of FIG. 7 or FIG. 8, instead of the width of the pulse output shown at (2) of each of FIGS. 2–5.

As set forth above, a light extinction type smoke detector employing pulsed light according to each of the two illustrated exemplary embodiments of the invention produces, due to a simple and appropriate arrangement, the effect that energy consumption is reduced by employing simple pulsed light or modulated pulsed light in place of continuous lighting and that smoke due to a fire and the interruption of a light path which extends from a light source to a photoelectric element or sensing the light of the light source are correctly discriminated from one another and detected, so that false alarms can be prevented.

We claim:
1. A light extinction type fire detector, comprising:
   a pulsed light-emitting element for emitting pulsed light;
   a photoelectric element for generating an output signal in response to light received from said transmitter;
   a transmission measurement path for the passage of smoke of a fire to be detected extending between said pulsed light-emitting element and said photoelectric element;
   a light path extending from said pulsed light-emitting element across said transmission measurement path to said photoelectric element;

the pulsed light emitted by said pulsed light-emitting element being attenuated by the smoke passing through said transmission measurement path;

a fire-detection circuit connected with said photoelectric element for discriminating whether said output signal of said photoelectric element is lower than a predetermined threshold value and for generating a fire-detection signal when said output signal of said photoelectric element is lower than said predetermined threshold value;

a false-alarm-prevention first time-delay circuit connected with said fire-detection circuit for generating a fire-alarm output signal when said fire-detection circuit generates said fire-detection signal for a first predetermined duration of time;

a second time-delay circuit connected with said fire-detection circuit for generating an inhibit signal when said fire-detection circuit generates said fire-detection signal for a second predetermined duration of time;

said first duration of time being at least as great as said second duration of time;

a light-path-interruption discriminating circuit connected with said photoelectric element for generating a light-path-interrupted signal when said output signal of said photoelectric element is lower than a predetermined threshold value for a third predetermined duration of time;

said third predetermined duration of time being less than said first predetermined duration of time and less than said second predetermined duration of time;

first inhibiting circuit means connected with said light-path-interruption discriminating circuit and with said second time-delay circuit for preventing said light-path-interruption discriminating circuit from generating said light-path-interrupted signal when said second time-delay circuit generates said inhibit signal; and second inhibiting circuit means connected with said fire-detection circuit and with said light-path-interruption discriminating circuit for preventing said fire-detection circuit from generating said fire-detection signal when said light-path-interruption discriminating circuit generates said light-path-interrupted signal.

2. A light extinction type smoke detector employing pulsed light, comprising:

a pulsed light-emitting element for emitting pulsed light;

a photoelectric element for sensing said pulsed light emitted by said pulsed light-emitting element;

said photoelectric element having an output side;

a transmission measurement path for the passage of smoke of a fire to be detected extending between said pulsed light-emitting element and said photoelectric element;

a light path extending from said pulsed light-emitting element across said transmission measurement path to said photoelectric element;

a peak-value hold circuit for generating a first output signal;

a fire-detection circuit indirectly connected through said peak-value hold circuit to said output side of the photoelectric element for generating a fire-detection signal when said first output signal is lower than a predetermined threshold value;

a light-path-interruption discriminating circuit directly connected to said output side of said photoelectric element;

said light-path-interruption discriminating circuit being provided for discriminating an interruption of said light path when a duration of said interruption attains a first prescribed time interval;

said light-path-interruption discriminating circuit being provided for generating a second output signal when said interruption is discriminated;

said output signal being provided for immediately inhibiting operation of said fire-detection circuit and for simultaneously initiating a light-path-interrupted signal;

said fire-detection circuit being provided for generating a fire-alarm signal when said fire detection signal has endured for a second prescribed time interval;

said fire-alarm signal being provided for inhibiting operation of said light-path-interruption discriminating circuit after a third prescribed time interval has elapsed; and said first, second and third prescribed time intervals having durations so interrelated that a duration of said second time interval is greater than a duration of said third time interval.

3. A light extinction type smoke detector employing pulsed light, comprising:

a modulated-pulsed light-emitting element for emitting modulated pulsed light;

a photoelectric element for sensing said modulated pulsed light emitted by said pulsed light-emitting element;

said photoelectric element having an output side;

a transmission measurement path for the passage of smoke of a fire to be detected extending between said modulated-pulsed light-emitting element and said photoelectric element;

a light path extending from said modulated-pulsed light-emitting element across said transmission measurement path to said photoelectric element;

an output wave-shaping circuit having an output;

a charge-discharge circuit for said output of said output wave-shaping circuit;

a peak-value hold circuit for generating a first output signal;

a fire-detection circuit indirectly connected through said peak-value hold circuit to said output side of said photoelectric element for generating a fire-detection signal when said first output signal is lower than a predetermined threshold value;

a light-path-interruption discriminating circuit indirectly connected through said output wave-shaping circuit and said charge-discharge circuit to said output side of the photoelectric element;

said light-path-interruption discriminating circuit being provided for discriminating an interruption of said light path when a duration of said interruption attains a first prescribed time interval;

said light-path-interruption discriminating circuit being provided for generating a second output signal when an interruption is discriminated;

said output signal being provided for immediately inhibiting operation of said fire-detection circuit and simultaneously initiating a light-path-interrupted signal;

said fire-detection circuit being provided for generating a fire-alarm signal when said fire-detection signal has endured for a second prescribed time interval;

said fire-alarm signal being provided for interdicting operation of said light-path-interruption discriminating circuit after a third prescribed time interval has elapsed;

said first, second and third prescribed time intervals having durations so interrelated that a duration of said second time interval is greater than a duration of said third time interval.

* * * * *